United States Patent
Niimi et al.

(10) Patent No.: US 11,517,769 B2
(45) Date of Patent: Dec. 6, 2022

(54) NEUTRON BEAM TRANSMISSION ADJUSTING DEVICE COMPRISING A NEUTRON BEAM TRANSMISSION UNIT INCLUDING A NEUTRON REACTANT, METHOD FOR PRODUCING NEUTRON BEAM TRANSMISSION ADJUSTING DEVICE, AND NEUTRON BEAM ADJUSTING METHOD

(71) Applicants: RICOH COMPANY, LTD., Tokyo (JP); NATIONAL UNIVERSITY CORPORATION TOKAI NATIONAL HIGHER EDUCATION AND RESEARCH SYSTEM, Nagoya (JP)

(72) Inventors: Tatsuya Niimi, Kanagawa (JP); Takashi Matsumura, Kanagawa (JP); Takuya Saito, Kanagawa (JP); Takeshi Kamomae, Nagoya (JP)

(73) Assignees: RICOH COMPANY, LTD., Tokyo (JP); NATIONAL UNIVERSITY CORPORATION TOKAI NATIONAL HIGHER EDUCATION AND RESEARCH SYSTEM, Nagoya (JP)

( * ) Notice: Subject to any disclaimer, the term of this patent is extended or adjusted under 35 U.S.C. 154(b) by 130 days.

(21) Appl. No.: 16/866,712

(22) Filed: May 5, 2020

(65) Prior Publication Data
US 2021/0008391 A1 Jan. 14, 2021

(30) Foreign Application Priority Data

Jul. 10, 2019 (JP) .............................. JP2019-128117
Mar. 31, 2020 (JP) .............................. JP2020-064293

(51) Int. Cl.
*A61N 5/10* (2006.01)
*G21K 5/04* (2006.01)

(52) U.S. Cl.
CPC ............. *A61N 5/1042* (2013.01); *A61N 5/10* (2013.01); *A61N 5/1064* (2013.01);
(Continued)

(58) Field of Classification Search
CPC ................... A61N 5/10; A61N 5/1042; A61N 2005/1085; A61N 2005/109;
(Continued)

(56) References Cited

U.S. PATENT DOCUMENTS 4,516,535 A * 5/1985 Russell, Jr. .......... A61K 41/009
250/518.1
5,392,319 A * 2/1995 Eggers ..................... H05H 3/06
376/151
(Continued)

FOREIGN PATENT DOCUMENTS

| JP | 2015-136895 | 7/2015 |
| JP | 2015-138192 | 7/2015 |
| JP | 2017-140417 | 8/2017 |

OTHER PUBLICATIONS

U.S. Appl. No. 16/601,846 dated Oct. 15, 2019.
(Continued)

*Primary Examiner* — Allen C. Ho
(74) *Attorney, Agent, or Firm* — Grüneberg and Myers, PLLC

(57) ABSTRACT

Provided is a neutron beam transmission adjusting device including a neutron beam transmission unit including a neutron reactant and capable of modulating an energy and/or a flux of a neutron beam transmitted through the neutron beam transmission unit.

17 Claims, 6 Drawing Sheets

(52) U.S. Cl.
CPC ......... *A61N 5/1065* (2013.01); *A61N 5/1067* (2013.01); *G21K 5/04* (2013.01); *A61N 2005/109* (2013.01); *A61N 2005/1085* (2013.01); *A61N 2005/1092* (2013.01); *A61N 2005/1095* (2013.01); *A61N 2005/1098* (2013.01)

(58) Field of Classification Search
CPC .... A61N 2005/1092; A61N 2005/1095; A61N 2005/1098; A61N 5/1064; A61N 5/1065; A61N 5/1067
USPC .......................................... 378/65; 250/518.1
See application file for complete search history.

(56) References Cited

U.S. PATENT DOCUMENTS

| | | | | |
|---|---|---|---|---|
| 5,433,693 | A * | 7/1995 | Ott | A61N 5/10 600/1 |
| 5,703,918 | A * | 12/1997 | Hiismaki | H05H 3/06 428/650 |
| 5,870,447 | A * | 2/1999 | Powell | H05H 6/00 376/194 |
| 5,903,622 | A * | 5/1999 | Yoon | H05H 3/06 376/110 |
| 5,920,601 | A * | 7/1999 | Nigg | G21K 5/04 376/194 |
| 6,130,926 | A * | 10/2000 | Amini | H05H 13/00 376/195 |
| 6,674,829 | B1 * | 1/2004 | Skold | A61N 5/10 376/346 |
| 9,636,524 | B2 * | 5/2017 | Pantell | A61N 5/1077 |
| 9,675,816 | B2 * | 6/2017 | Kuri | H05H 3/06 |
| 9,789,340 | B2 * | 10/2017 | Liu | A61N 5/1077 |
| 9,868,673 | B2 * | 1/2018 | Furuya | A61P 35/00 |
| 9,889,320 | B2 * | 2/2018 | Liu | H05H 6/00 |
| 9,974,979 | B2 * | 5/2018 | Liu | A61N 5/1077 |
| 10,155,123 | B2 * | 12/2018 | Mukawa | A61N 5/103 |
| 10,157,693 | B2 * | 12/2018 | Liu | A61N 5/10 |
| 10,239,895 | B2 * | 3/2019 | Liu | A61K 41/0095 |
| 10,328,286 | B2 * | 6/2019 | Liu | C04B 35/553 |
| 10,343,951 | B2 * | 7/2019 | Furuya | A61N 5/10 |
| 10,434,333 | B2 * | 10/2019 | Liu | A61N 5/10 |
| 10,441,815 | B2 * | 10/2019 | Akahori | G01T 1/161 |
| 10,442,181 | B2 * | 10/2019 | Iwata | A61L 15/60 |
| 10,462,893 | B2 * | 10/2019 | Park, Jr. | G21G 4/02 |
| 10,470,289 | B2 * | 11/2019 | Tsuchida | B23K 20/021 |
| 10,525,285 | B1 * | 1/2020 | Friedman | G01T 1/40 |
| 10,537,750 | B2 * | 1/2020 | Liu | A61N 5/1049 |
| 10,568,964 | B2 * | 2/2020 | Yamaguchi | A61N 5/1031 |
| 10,584,194 | B2 * | 3/2020 | Iwata | C08J 3/075 |
| 10,589,125 | B2 | 3/2020 | Niimi et al. | |
| 10,639,499 | B2 * | 5/2020 | Liu | G21K 1/067 |
| 10,709,783 | B2 * | 7/2020 | Liu | A61N 5/10 |
| 10,773,104 | B2 * | 9/2020 | Liu | G21K 1/02 |
| 10,791,618 | B2 * | 9/2020 | Hsueh Liu | H05H 7/001 |
| 10,882,245 | B2 * | 1/2021 | Iwata | B33Y 30/00 |
| 10,898,731 | B2 * | 1/2021 | Liu | A61N 5/1077 |
| 10,898,733 | B2 * | 1/2021 | Liu | H05H 6/00 |
| 10,926,108 | B2 * | 2/2021 | Liu | A61N 5/1042 |
| 10,926,110 | B2 * | 2/2021 | Liu | A61N 5/1048 |
| 10,950,143 | B2 * | 3/2021 | Niimi | B33Y 70/00 |
| 10,994,154 | B2 * | 5/2021 | Liu | B33Y 80/00 |
| 11,024,437 | B2 * | 6/2021 | Park, Jr. | G21G 4/02 |
| 11,058,898 | B2 * | 7/2021 | Liu | A61N 5/1077 |
| 11,062,814 | B1 * | 7/2021 | Usui | G21F 3/00 |
| 11,179,464 | B2 * | 11/2021 | Heibel | A61K 41/0095 |
| 11,198,023 | B2 * | 12/2021 | Chen | G21K 5/04 |
| 11,224,766 | B2 * | 1/2022 | Liu | G21K 5/04 |
| 11,266,859 | B2 * | 3/2022 | Liu | H05H 3/06 |
| 11,324,967 | B2 * | 5/2022 | Heibel | A61N 5/1048 |
| 11,338,155 | B2 * | 5/2022 | Hsiao | A61N 5/1049 |
| 11,400,314 | B2 * | 8/2022 | Hsiao | A61N 5/1001 |
| 11,400,316 | B2 * | 8/2022 | Liu | C04B 41/84 |
| 2016/0158578 | A1 | 6/2016 | Liu et al. | |
| 2016/0158579 | A1 | 6/2016 | Liu et al. | |
| 2017/0008228 | A1 | 1/2017 | Iwata et al. | |
| 2017/0022348 | A1 | 1/2017 | Iwata et al. | |
| 2017/0369607 | A1 | 12/2017 | Iwata et al. | |
| 2018/0061279 | A1 | 3/2018 | Niimi et al. | |
| 2018/0126651 | A1 | 5/2018 | Matsumura et al. | |
| 2018/0345574 | A1 | 12/2018 | Matsumura et al. | |
| 2019/0010259 | A1 | 1/2019 | Iwata et al. | |
| 2019/0381784 | A1 | 12/2019 | Iwata et al. | |
| 2020/0071432 | A1 | 3/2020 | Matsumura et al. | |

OTHER PUBLICATIONS

T. Kamomae, et al., Development of Three-Dimensional Printed Compensator for Improvement of Dose Distribution in Boron Neutron Capture Therapy: A Preliminary Study, AAPM 61st. Annual Meeting & Exhibition—Meeting Program—Abstract Information.
Yoshinori Sakurai, et al., Physics in Medicine & Biology, 52 (2007) 7409-7422.

* cited by examiner

NEUTRON BEAM TRANSMISSION ADJUSTING DEVICE COMPRISING A NEUTRON BEAM TRANSMISSION UNIT INCLUDING A NEUTRON REACTANT, METHOD FOR PRODUCING NEUTRON BEAM TRANSMISSION ADJUSTING DEVICE, AND NEUTRON BEAM ADJUSTING METHOD

CROSS-REFERENCE TO RELATED APPLICATIONS

The present application claims priority under 35 U.S.C. § 119 to Japanese Patent Application No. 2019-128117 filed Jul. 10, 2019, and Japanese Patent Application No. 2020-064293 filed Mar. 31, 2020. The contents of which are incorporated herein by reference in their entirety.

BACKGROUND OF THE INVENTION

Field of the Invention

The present disclosure relates to a neutron beam transmission adjusting device, a method for producing a neutron beam transmission adjusting device, and a neutron beam adjusting method.

Description of the Related Art

The neutron capture therapy is a therapy using, for example, a nuclear reactor or an accelerator to irradiate tumor cells with neutron beams having a relatively low energy. In the neutron capture therapy, tumor cells are previously let to take in a radiosensitizer such as boron or gadolinium compounds, and the radiosensitizers in the tumor cells are irradiated with neutron beams from the outside the body.

In the neutron capture therapy, a nuclear reaction occurs between the neutron beams and the radiosensitizer in the tumor cells, and the tumor cells that have taken in the radiosensitizer can be selectively killed by, for example, alpha rays generated from the nuclear reaction.

Specifically, for example, a boron-containing compound is used as the radiosensitizer and is selectively taken into tumor cells. Alpha rays and a $^7Li$ particle that are generated from a nuclear reaction between the boron compound and neutrons can only pass a distance that is about the same as the diameter of a cell (about 10 micrometers). Therefore, in the neutron capture therapy, the tumor cells that take in an abundance of a boron compound can be damaged significantly and killed with alpha rays and a $^7Li$ particle generated from a nuclear reaction between the boron and neutrons, while damage on normal cells that take in almost no boron compound is suppressed.

In the neutron capture therapy, fast neutrons extracted from, for example, a nuclear reactor or an accelerator and having an energy of 10 keV or higher are converted to epithermal neutrons having an energy of about from 0.5 keV through 10 keV using an attenuating device, and a human body (target volume) is irradiated with the epithermal neutrons (for example, see Japanese Unexamined Patent Application Publication No. 2017-140417).

However, in the neutron capture therapy according to existing techniques, neutron beams having a uniform energy and a uniform flux are irradiated to tumor cells. Therefore, the tolerance dose of normal tissues surrounding the tumor cells may have been exceeded, or the sufficient therapeutic effect on the tumor cells may not have been satisfactory.

SUMMARY OF THE INVENTION

According to one aspect of the present disclosure, a neutron beam transmission adjusting device includes a neutron beam transmission unit comprising a neutron reactant and capable of modulating the energy and/or the flux of a neutron beam that is transmitted through the neutron beam transmission unit.

DESCRIPTION OF THE EMBODIMENTS

Figure 1:
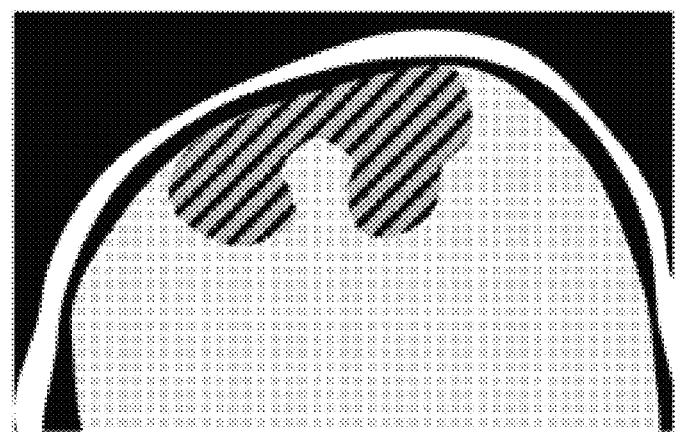
FIG. 1 is an example view modeling a computed tomography (CT) image captured from around a tumor tissue.

Unless otherwise defined herein, all technical terms and scientific terms used herein have the same meanings as ordinarily understood by persons skilled in the art. All patents, patent applications, published applications, and other publications referred to herein are incorporated herein by reference in their entirety. If there is any contradiction between descriptions in the documents referred to herein and descriptions herein, the descriptions herein should be prioritized.

(Neutron Beam Transmission Adjusting Device)

A neutron beam transmission adjusting device of the present disclosure includes a neutron beam transmission unit comprising a neutron reactant and capable of modulating the energy and/or the flux of a neutron beam that is transmitted through the neutron beam transmission unit, and further includes other members (units) as needed.

The present disclosure has an object to provide a neutron beam transmission adjusting device that can have neutron beams that have been transmitted through the device modulated to desired characteristics.

The present disclosure can provide a neutron beam transmission adjusting device that can have neutron beams that have been transmitted through the device modulated to desired characteristics.

In one aspect, the neutron beam transmission adjusting device of the present disclosure is provided. It is known in the art that the existing techniques cannot modulate neutron beams to have desired characteristics.

More specifically, in one aspect, the present disclosure is based on the following finding. Because existing techniques relating to the neutron capture therapy irradiated neutron beams having a uniform energy and a uniform flux toward tumor cells, the tolerance dose of normal tissues surrounding the tumor cells may be exceeded. Existing techniques relating to the neutron capture therapy may fail to have a sufficient therapeutic effect, since the energy the neutron beams reaching the tumor cells may be extremely high depending on the shape or position of the tumor and the neutron beams may pass through the tumor without interacting with the radiosensitizer. Hence, the neutron capture therapy, which is one suitable application of the neutron beam transmission adjusting device of the present disclosure, is described hereinbelow.

The neutron capture therapy is a cancer therapy that treats tumor cells, which have taken in a radiosensitizer, with neutron beams such as thermal neutron beams or epithermal neutron beams.

The lesional cell to be treated by the neutron capture therapy is not particularly limited and may be appropriately selected depending on the intended purpose so long as the lesional cell can take in a radiosensitizer and can be exposed to neutron beams. Examples of the lesional cell include a tumor cell. In the present disclosure, "tumors" include benign tumors such as polyps and malignant tumors such as cancers. Malignant tumors are preferable. In the present disclosure, "cancers" include cancers of epithelial origin (carcinoma), sarcoma, and hematological malignancies.

Unless otherwise specified herein, cases where the radiosensitizer is boron (may be referred to as boron neutron capture therapy (BNCT)) will be described. However, this is not meant to limit the scope of the present disclosure, but is meant to facilitate understanding. The description in the present specification is also applicable to cases where other radiosensitizers are used.

In usual the tumor cells are metabolically active compared to normal cells and have the property that proactively take in a radiosensitizer injected in vivo by, for example, intravenous drip. In the neutron capture therapy, the radiosensitizer is taken in by tumor cells utilizing the property. Next, in the neutron capture therapy, neutron beams are irradiated to the tumor cells, to be allowed to undergo a nuclear reaction with the radiosensitizer. Through the nuclear reaction, the radiosensitizer (boron atom) generates alpha (α) rays and a $^7Li$ particle. The alpha rays and the $^7Li$ particle generated give a significant damage to the tumor cells, and kill the tumor cells. Here, because the alpha rays and the $^7Li$ particle can only pass through about 10 micrometers, what can be killed are only the tumor cells that have taken in the radiosensitizer, making it possible to selectively kill the tumor cells. Further, in the typical radiation therapy, there is a need for performing radiation exposure some tens of times (a period of about from one month through two months is needed), whereas in the neutron capture therapy, the treatment is often completed with one exposure, providing an advantage that the patient is less burdened.

In the neutron capture therapy according to existing techniques, neutrons generated from a nuclear reactor or an accelerator are typically used as neutron beams. Such neutrons have an energy of 10 keV or higher, and are referred to as fast neutrons. In the neutron capture therapy, the energy of the fast neutrons is attenuated with, for example, a moderator, to convert the fast neutrons to epithermal neutrons having an energy of about from 0.5 keV through 10 keV. Here, the moderator used has a function of decelerating the neutron energy and a function of selecting the uniform neutron energy beam.

Subsequently, in the neutron capture therapy, tumor cells of a patient are irradiated with the epithermal neutrons obtained. The irradiant epithermal neutrons are scattered and decelerated by, for example, hydrogen in the patient body, and the irradiated neutron energy is gradually decreased and converted to thermal neutrons of 0.5 eV or lower. The thermal neutrons reach the tumor cells and undergo a nuclear reaction with the radiosensitizer (boron atom). Alpha rays and a $^7Li$ particle generated from the nuclear reaction thus selectively kill the tumor cells.

In the neutron capture therapy according to existing techniques, when irradiating the tumor cells (target region or lesion site) of a patient with thermal neutron beams or epithermal neutron beams generated from a nuclear reactor or an accelerator, the thermal neutron beams or the epithermal neutron beams are collimated to the selected lesion site with, for example, a collimator. Hence, in the neutron capture therapy according to existing techniques, normal tissues and the lesion site or tumor region are uniformly irradiated with the same neutron beam flux. Hence, in the neutron capture therapy according to existing techniques, the tolerance dose of the normal tissue surrounding the tumor cells may be exceeded.

Further, as described above, in the neutron capture therapy according to existing techniques, epithermal neutron energy is gradually decreased due to the influence of, for example, hydrogen in the patient body. And the epithermal neutrons are converted to thermal neutrons, and, and then thermal neutrons interact with the radiosensitizer taken into the tumor cells. Therefore, depending on, for example, the shape or position of the target volume, the energy of the irradiated epithermal neutron beams may not be sufficiently decreased and the neutron beam may have excessively high energy when the epithermal neutron beams reach the tumor cells, the neutron beams may pass through without interacting with the radiosensitizer and it leads to make less therapeutic effect.

Moreover, in any other applications of neutron beams than the neutron capture therapy, the characteristics of the uniform neutron beams irradiated cannot be sufficiently controlled, and the neutron beam irradiation accuracy may be poor.

Hence, the present inventors have found that the existing techniques have the problems described above because, for example, irradiant neutron beams have uniform characteristics such as flux.

Hence, the present inventors have repeated earnest studies into, for example, devices capable of having neutron beams that have been transmitted through the devices modulated to desired characteristics, and conceived of the present disclosure. That is, the present inventors have found that a neutron beam transmission adjusting device including a neutron beam transmission unit including a neutron reactant and capable of modulating the energy and/or the flux of neutron beams to be transmitted through the device can have neutron beams that have been transmitted through the device modulated to desired characteristics.

Here, as described above, the neutron beam transmission adjusting device of the present disclosure is preferably used in the neutron capture therapy. When the neutron beam transmission adjusting device of the present disclosure is used in the neutron capture therapy, in a more preferable embodiment, the neutron beam transmission adjusting device can optimally modulate the energy and/or the flux of neutron beams to be irradiated to about the lesion site in accordance with, for example, the condition of the lesion site (e.g., the shape of the lesion site), the shape of the body surface at a portion to be irradiated, and the shape of organs surrounding the lesion site. In other words, the neutron beam transmission adjusting device of the present disclosure can appropriately modulate the energy and/or the flux of neutron beams to be irradiated to each patient (to be transmitted through the device) in accordance with, for example, the condition of the patient (therapy target). Hence, the neutron beam transmission adjusting device of the present disclosure can control the energy and the flux of neutron beams to be irradiated to lesional cells in accordance with, for example, the condition of the patient (therapy target), in a manner that the therapeutic effect is enhanced and damages on the surrounding areas due to exposure are minimized. Therefore, it is preferable that the neutron beam transmission adjusting device of the present disclosure used in the neutron capture therapy be installed between a collimator and a therapy target.

A method of use of the neutron beam transmission adjusting device of the present disclosure when used in the neutron capture therapy will be described with reference to the drawings.

FIG. 1 is an example view modeling a computed tomography (CT) image captured from around a tumor tissue. As illustrated in FIG. 1, the tumor tissue (shaded area), which is the therapy target in the neutron capture therapy, may have a complicated shape.

Figure 2A:
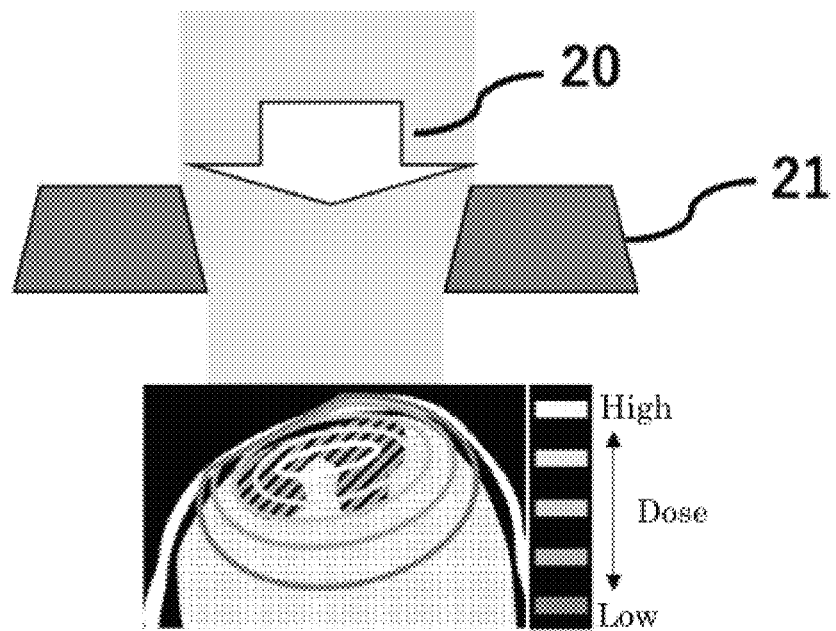
FIG. 2A is an exemplary view illustrating an example state of neutron beam irradiation in the neutron capture therapy according to an existing technique.

In the neutron capture therapy according to existing techniques, for example, the tumor tissue is irradiated with neutron beams 20 collimated with a collimator 21 as illustrated in FIG. 2A. FIG. 2A illustrates the amount (dose) of the neutron beams 20 that reach the tissue when the neutron beams are irradiated, as a contour map.

In the neutron capture therapy according to existing techniques, because uniform neutron beams 20 are irradiated, the tolerance dose of normal tissues surrounding the tumor tissue may be exceeded and damages due to exposure may be unnecessarily given to the normal tissues. In the example of FIG. 2A, as can be seen from the contour map illustrating an example of the dose of neutron beams 20 that reach the tissue, neutron beams 20 are irradiated in relatively high doses to the normal tissues (checkered area) other than the tumor tissue.

Moreover, in the neutron capture therapy according to existing techniques, when the target is a tumor tissue having a complicated shape as illustrated in FIG. 1 and FIG. 2A, depending on the part of the tumor tissue, the neutron beams may have an extremely high energy when reaching the tumor cells and pass through without interacting with the radiosensitizer, to fail to be sufficiently therapeutically effective.

Figure 2B:
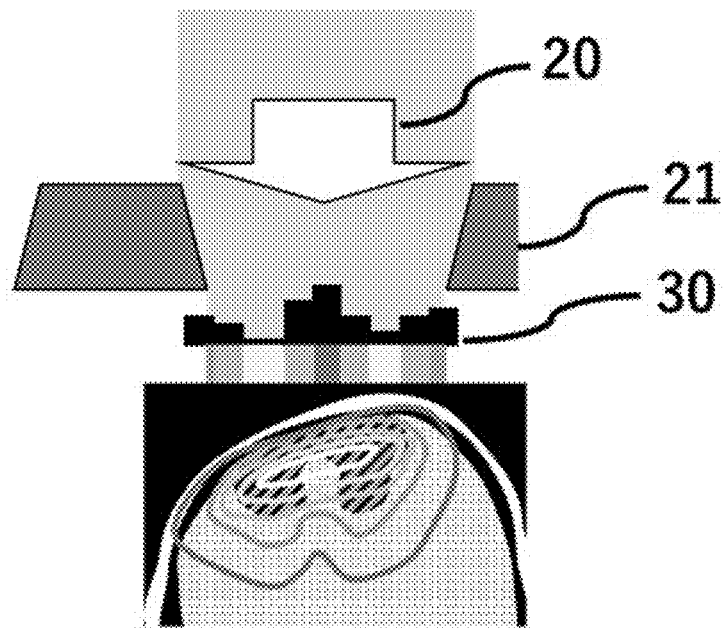
FIG. 2B is an exemplary view illustrating an example state of neutron beam irradiation in the neutron capture therapy using an example of a neutron beam transmission adjusting device of the present disclosure.

FIG. 2B illustrates an example when the neutron beam transmission adjusting device 30 of the present disclosure is used in the neutron capture therapy. In the example illustrated in FIG. 2B, the neutron beam transmission adjusting device of the present disclosure is disposed between a collimator and a tumor tissue, to modulate the characteristics of neutron beams to be transmitted through the neutron beam transmission adjusting device. FIG. 2B illustrates an irradiation distribution (distribution of characteristics) of neutron beams after transmitted and modulated through the neutron beam transmission adjusting device, by gradation.

In the example of FIG. 2B, the energy and the flux of neutron beams are modulated in accordance with, for example, the shape of the tumor tissue, and the flux of neutron beams irradiated to the normal tissues is controlled. Moreover, in the example of FIG. 2B, when the neutron beams reach the tumor cells, the energy and the flux of the neutron beams have been modulated in accordance with, for example, the shape of the tumor tissue. Therefore, the neutron beams are facilitated to interact with the radiosensitizer taken into the tumor tissue and the tumor tissue is irradiated with the neutron beams of an appropriate flux.

Figure 2C:
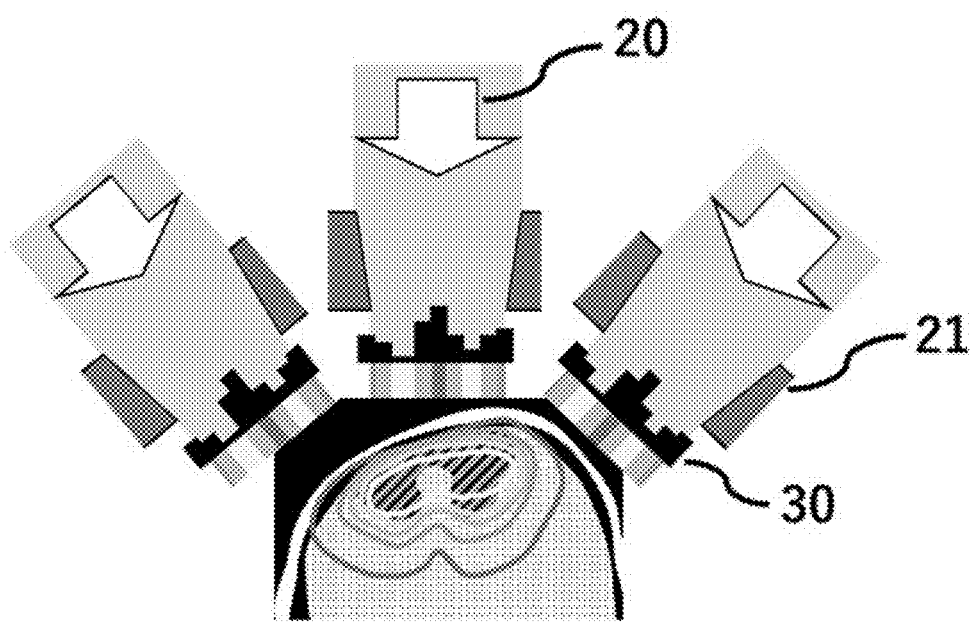
FIG. 2C is an exemplary view illustrating another example state of neutron beam irradiation in the neutron capture therapy using an example of a neutron beam transmission adjusting device of the present disclosure.

FIG. 2C illustrates another example when the neutron beam transmission adjusting device of the present disclosure is used in the neutron capture therapy. The example illustrated in FIG. 2C is an example where a plurality of neutron beam sources are configured to irradiate neutron beams to a tumor tissue (for multiple field irradiation), so the neutron beam transmission adjusting device of the present disclosure is disposed at respective positions between a collimator and the tumor tissue.

In the example of FIG. 2C, the energy and the flux of neutron beams are modulated in accordance with, for example, the shape of the tumor tissue, and the flux of neutron beams to be irradiated to the normal tissues is suppressed. Moreover, in the example of FIG. 2C, when the neutron beams reach the tumor cells, the energy and the flux of the neutron beams have been modulated in accordance with, for example, the shape of the tumor tissue, so the neutron beams are facilitated to interact with the radiosensitizer taken into the tumor tissue and the tumor tissue is irradiated with the neutron beams of a more appropriate flux.

FIG. 2C illustrates an example where one neutron beam transmission adjusting device is used for one collimator. However, this is non-limiting. For example, the neutron beam transmission adjusting device may be used for only one collimator among a plurality of collimators.

When using the neutron beam transmission adjusting device of the present disclosure in the neutron capture therapy, the neutron beam transmission adjusting device is used, with the device installed between the neutron beam source and the tumor tissue (lesion site) as illustrated in FIG. 2B and FIG. 2C. The installation position of the neutron beam transmission adjusting device is not particularly limited, and may be a position between the neutron beam source and the irradiation target to be irradiated with neutron beams. More specific examples of the installation position of the neutron beam transmission adjusting device include an immediately succeeding position of a collimator (at the irradiation target side), and a position on the body surface of a patient, who is the therapy target. Moreover, because neutron beams irradiated from a plurality of neutron beam sources (neutron beam irradiating devices) are typically collimated to about the lesion site, one neutron beam transmission adjusting device may be installed at a position close to the lesion site so that the neutron beams from the plurality of neutron beam sources may be collectively modulated.

When the neutron beam transmission adjusting device of the present disclosure is used in the neutron capture therapy, in order to modulate the neutron beams in accordance with, for example, the shape of the lesion site as illustrated in FIG. 2B and FIG. 2C, for example, it is preferable that the neutron beam transmission unit of the neutron beam transmission adjusting device be configured to perform modulation in accordance with the conditions of the lesion site of the irradiation target (for example, a patient).

Here, the conditions of the lesion site mean the physical conditions of the lesion site affecting modulation of neutron beams, such as the shape of the lesion site, the shapes of organs surrounding the lesion site, the depth of the lesion site from the body surface, and the shape of the body surface at a position at which the lesion site exists.

In the present disclosure, lesion site condition data means data including information on the conditions of the lesion site. The lesion site condition data can be obtained based on, for example, medical data such as CT data and MRI data of the irradiation target (patient).

That is, when the neutron beam transmission adjusting device of the present disclosure is used in the neutron capture therapy, it is preferable that the neutron beam transmission adjusting device be used with the device disposed between the neutron beam source and the irradiation target to be irradiated with neutron beams on the neutron beam path, and that the neutron beam transmission unit be configured to perform modulation in accordance with the conditions of the lesion site of the irradiation target. This makes it possible to appropriately control the energy and/or the flux of the neutron beams, improve the therapeutic effect of the neutron capture therapy, and suppress neutron beams to be irradiated to normal tissues surrounding the lesion site.

The neutron beam transmission unit included in the neutron beam transmission adjusting device of the present disclosure will be described below more specifically.

<Neutron Beam Transmission Unit>

The neutron beam transmission unit is not particularly limited and may be appropriately selected depending on the intended purpose, so long as the neutron beam transmission unit includes a neutron reactant and can modulate the energy and/or the flux of neutron beams to be transmitted through the neutron beam transmission unit.

Furthermore, as described above, the neutron beam transmission adjusting device of the present disclosure is not particularly limited so long as the neutron beam transmission adjusting device includes the neutron beam transmission unit. For example, the neutron beam transmission adjusting device may be entirely formed of the neutron beam transmission unit, or may be partially formed of the neutron beam transmission unit. In the present disclosure, in terms of productivity, it is preferable that the neutron beam transmission adjusting device be entirely formed of the neutron beam transmission unit.

<<Neutron Reactant>>

The neutron reactant (or neutron reactant material) means a substance that can adjust (modulate) the energy or the flux of neutron beams to be transmitted through the neutron beam transmission unit. For example, the neutron reactant needs at least to be able to scatter neutron beams when adjusting the energy of the neutron beams, and needs at least to be able to capture (absorb) neutron beams when adjusting the flux of the neutron beams. Hence, specifically, the neutron reactant of the present disclosure may be a substance that is capable of scattering and/or absorbing the neutron beams.

It is preferable that the neutron reactant be a substance (atom) having a large neutron interaction cross-section. The neutron interaction cross-section is a quantity that expresses a probability that the substance scatters or absorbs neutrons when the neutrons impinge on the atomic nucleus of the atom constituting the substance. The larger the neutron interaction cross-section, the more likely the substance is to scatter or absorb neutrons.

Examples of substances (atoms) having a large neutron interaction cross-section include a boron atom (B: for example, 10B), a lithium atom (Li: for example, $^6$Li), and a gadolinium atom (Gd: for example, $^{155}$Gd, and $^{157}$Gd). In other words, in the present disclosure, it is preferable that the neutron reactant contain at least any one selected from a boron atom, a lithium atom, and a gadolinium atom. Because a neutron reactant that contains any of these atoms can adjust the energy or the flux of neutron beams easily, the neutron beams that have been transmitted through the neutron reactant can be modulated to desired characteristics more easily.

Examples of a compound containing a boron atom and applicable as the neutron reactant include borates, metaborates, oxides, nitrides, sulfides, and halides.

Examples of a compound containing a lithium atom and applicable as the neutron reactant include: salts such as lithium carbonate, lithium acetate, lithium nitrate, and trilithium citrate; halides such as lithium fluoride and lithium iodide; double oxides such as lithium oxide, lithium hydroxide, sulfides, nitrides, lithium tantalate, and lithium titanate; and silicate minerals such as clay (montmorillonite and hectorite), Jadarite, and spodumene.

Examples of a compound containing a gadolinium atom and applicable as the neutron reactant include: salts such as gadolinium chloride, gadolinium carbonate, gadolinium sulfate, and gadolinium nitrate (all of these salts are hydrates); oxides; nitrides; halides; and gadolinium complexes.

These compounds may be used alone or in combination.

<<Modulation of Neutron Beams>>

In the present disclosure, "modulating" neutron beams means changing the characteristics of the neutron beams such as the energy, the flux (dose), and the distribution of the neutron beams. Hence, in the present disclosure, although modulating the neutron beams also includes increasing the energy or the flux of the neutron beams, it is preferable to modulate the energy or the flux of the neutron beams in the direction toward reduction when the invention of the present disclosure is used in the neutron capture therapy.

Neutron beams that are transmitted through the neutron beam transmission unit of the neutron beam transmission adjusting device of the present disclosure interact with the neutron reactant materials, and the neutron energy or the neutron flux is modulated as a result. The method for controlling the modulation degree of the neutron beams transmitted through the neutron beam transmission unit is not particularly limited and may be appropriately selected depending on the intended purpose. In a preferable embodiment, examples of the method include providing the neutron beam transmission unit with a thickness distribution, providing the neutron reactant with a concentration distribution, and combination of these methods.

As described above, in the present disclosure, it is preferable that the neutron beam transmission unit have a thickness distribution. In the present disclosure, the phrase "the neutron beam transmission unit has a thickness distribution" means that the thickness of the neutron beam transmission unit in the neutron beam transmission direction varies from position to position. The longer the distance traveled by the neutron beams through the neutron beam transmission unit in the neutron transmission direction (i.e., the greater the thickness of the neutron beam transmission unit), the more likely the neutrons interact with the neutron reactant. Therefore, it is inferred that the neutron energy and/or the flux of the neutrons can be reduced.

When the neutron beam transmission unit has a thickness distribution, the sample shape of the neutron beam transmission adjusting device is as illustrated in FIG. 2B. In this case, in the present disclosure, it is preferable to control the thickness distribution of the neutron beam transmission unit in a manner that the neutron beam energy, the neutron beam flux, and the dose distribution calculated based on the patient data including the target region or lesion site will be obtained. In this case, the neutron beam transmission unit may be formed of, for example, a homogeneous material, more specifically, a material that makes the neutron reactant concentration constant.

Further, in the present disclosure, for example, it is preferable that the neutron beam transmission unit have a neutron reactant concentration distribution. When it is said that the neutron beam transmission unit has a neutron reactant concentration distribution, it is meant that the concentration of the neutron reactant in the neutron beam transmission unit varies from position to position. The higher the concentration of the neutron reactant at a position to be passed by a neutron beam in the neutron beam transmission unit in the neutron transmission direction, the more likely the neutrons are to interact with the neutron reactant. Therefore, it is inferred that the energy and/or the flux of the neutron beams can be reduced more securely. In this case, in the present disclosure, it is preferable to control the neutron reactant concentration distribution in the neutron beam transmission unit in a manner that the energy, the dose, and the distribution of neutron beams calculated based on the lesion site condition data of a therapy target (irradiation target) will be obtained. In this case, in the present disclosure, for example, the thickness of the neutron beam transmission unit may be constant, whereas the neutron reactant may have a concentration distribution.

Furthermore, as described above, in the present disclosure, it is naturally possible to modulate neutron beams to be transmitted through the neutron beam transmission unit by varying both of the thickness of the neutron beam transmission unit and the concentration of the neutron reactant.

<<Material and Shape>>

The material of the neutron beam transmission unit is not particularly limited and may be appropriately selected depending on the intended purpose, so long as the material contains the neutron reactant and neutron beams can be transmitted through the material.

The shape of the neutron beam transmission unit is not particularly limited and may be appropriately selected depending on the intended purpose.

For example, the present disclosure includes the following two preferable modes of the material and the shape of the neutron beam transmission unit.

In the first mode (mode 1), a container is filled with a material containing the neutron reactant. Specifically, a container is produced in a manner to have a hollow structure having a thickness distribution that provides energy and flux distributions of neutron beams, calculated based on the lesion site condition data of a therapy target patient, and the container is filled with the material (for example, a liquid or a solid) containing the neutron reactant.

The container is not particularly limited so long as neutron beams can be transmitted through the container. A material that has a small neutron interaction cross-section can be used. For example, ordinary resins can be used. The container can be produced according to a known method in the art.

In the second mode (mode 2), the neutron reactant is mixed with a self-standing material. In this embodiment, both of the following methods can be used as the method for modulating neutron beams: controlling the thickness distribution; and controlling the neutron reactant concentration distribution.

In the case of controlling the thickness distribution, for example, a basic structure is formed based on the lesion site condition data, and the neutron reactant is homogeneously mixed with the basic structure.

In the case of controlling the neutron reactant concentration distribution, a neutron reactant concentration distribution is formed in a basic structure having a constant thickness. The method for forming a neutron reactant concentration distribution is not particularly limited, and for example, any method commonly known in the art can be used. For example, a three-dimensional object producing apparatus (three-dimensional printer) of an inkjet method including a material jetting method can be used to form a neutron reactant concentration distribution.

In any of these embodiments, any material can be used as the material of the neutron beam transmission unit. Preferably, a common material such as a resin having a small neutron interaction cross-section can be used.

In the present disclosure, it is preferable that the neutron beam transmission unit be deformable. When the neutron beam transmission unit is deformable, the shape of at least part of the neutron beam transmission unit needs at least to be deformable. The degree of deformation is not particularly limited, so long as the flux and the energy of neutron beams to be modulated are not changed beyond a tolerable range from desired degrees of modulation.

In the present disclosure, the neutron beam transmission unit that is deformable can be shaped in a manner to conform to the body surface of an irradiation target (patient). More specifically, for example, when using the neutron beam transmission adjusting device in contact with a patient serving as an irradiation target, a soft material such as a rubber and gel may be used as the neutron beam transmission unit, to make the neutron beam transmission unit closely adhesive to the body surface of the patient, and to shape the neutron beam transmission unit to conform to the body surface. In this way, supporting and fastening of the neutron beam transmission adjusting device are more facilitated.

In the present disclosure, it is also preferable that the shape of the neutron beam transmission adjusting device be shaped to conform to the body surface of a patient. In other words, in the present disclosure, it is preferable that the neutron beam transmission adjusting device have a shape conforming to the surface (body surface) of a neutron beam irradiation target (patient). In this case, for example, it is preferable to obtain body surface profile data (e.g., bumps and dents on/in the surface) of a neutron beam irradiation part of the patient, and shape one side of the neutron beam transmission adjusting device in a manner to fit the body surface based on the obtained body surface profile data.

In this way, in the neutron beam transmission adjusting device of the present disclosure, for example, it is preferable that the neutron beam transmission unit have a thickness distribution and/or a neutron reactant concentration distribution corresponding to each patient's lesion site condition, and also that the neutron beam transmission unit be deformable in a manner to conform to the body surface of the patient. For example, such a neutron beam transmission adjusting device can be realized based on made-to-order production based on the patient's lesion site condition data using a deformable soft material. When producing the neutron beam transmission adjusting device in accordance with the patient's lesion site condition data, for example, it is preferable to use a three-dimensional object producing apparatus suitable for formation of a complicated shape and small-lot production.

In consideration of the above, it is preferable that the material of the neutron beam transmission unit of the neutron beam transmission adjusting device of the present disclosure be a material that satisfies, for example, the following three conditions.

(1) To contain a neutron reactant
(2) To be self-standing (shape-retainable)
(3) To be used for production with a three-dimensional object producing apparatus Examples of the material that satisfies the above three conditions include a gelation material. The following hydrogel is particularly preferable as the gelation material.

—Hydrogel—

It is preferable that the hydrogel used in the neutron beam transmission adjusting device of the present disclosure contain water, a polymer, and a mineral. In other words, it is preferable that the neutron beam transmission unit in the neutron beam transmission adjusting device of the present disclosure contain a hydrogel containing water, a polymer, and a mineral. Particularly, it is preferable that the hydrogel contain water in a three-dimensional network structure formed by a mineral dispersed in an organic solvent being combined with a polymer produced from polymerization of a polymerizable monomer. The hydrogel may also contain a neutron reactant and other components as needed.

The hydrogel can be obtained by, for example, dispersing and mixing the materials described below by an appropriate method to prepare an ink in the form of a hydrogel precursor, and curing the ink by an appropriate method. The materials of the hydrogel precursor will be described below.

—Water—

For example, pure water such as ion-exchanged water, ultrafiltrated water, reverse osmotic water, and distilled water, and ultrapure water can be used as the water. Any other component such as an organic solvent may be dissolved or dispersed in the water with a view to, for example, imparting a moisture retaining property, imparting an antimicrobial activity, imparting conductivity, and adjusting hardness.

—Mineral—

The mineral is not particularly limited and may be appropriately selected depending on the intended purpose. Examples of the mineral include a water-swellable layered clay mineral.

Figure 5:
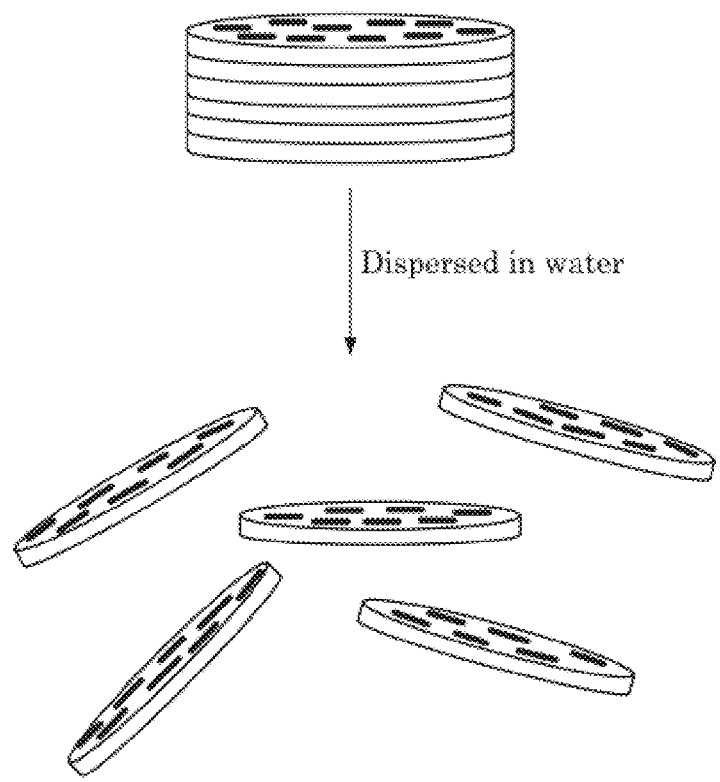
FIG. 5 is an exemplary view illustrating an example of a layered clay mineral and a dispersed state of the layered clay mineral in water.

The water-swellable layered clay mineral has a state wherein two-dimensional discoid crystals including a unit lattice in the crystals are stacked as illustrated in the upper section of FIG. 5 illustrating a state of single layers being dispersed in water. When the water-swellable layered clay mineral is dispersed in water, the crystals are separated into single-layer forms to become discoid crystals as illustrated in the lower section of FIG. 5.

Examples of the water-swellable layered clay mineral include water-swellable smectite and water-swellable mica. More specific examples of the water-swellable layered clay mineral include water-swellable hectorite containing sodium as an interlayer ion, water-swellable montmorillonite, water-swellable saponite, and water-swellable synthetic mica. One of these water-swellable layered clay minerals may be used alone or two or more of these water-swellable layered clay minerals may be used in combination. Among these water-swellable layered clay minerals, water-swellable hectorite including a Li atom having a large neutron interaction cross-section in the structure is preferable.

The water-swellable hectorite may be an appropriately synthesized product or a commercially available product. Examples of the commercially available product include synthetic hectorite (LAPONITE XLG, available from Rock Wood), SWN (available from Coop Chemical Ltd.), and fluorinated hectorite SWF (available from Coop Chemical Ltd.). Among these commercially available products, synthetic hectorite is preferable in terms of the hardness and the elastic modulus of the neutron beam transmission adjusting device of the present disclosure.

Water-swellability means that a layered clay mineral is dispersed in water when water molecules are inserted between layers of the layered clay mineral as illustrated in FIG. 5.

The content of the water-swellable layered clay mineral is not particularly limited, may be appropriately selected depending on the intended purpose, and is preferably from 1% by mass through 40% by mass relative to the total amount of the materials constituting the neutron beam transmission adjusting device.

—Polymer—

Examples of the polymer include polymers containing an amide group, an amino group, a hydroxyl group, a tetramethyl ammonium group, a silanol group, and an epoxy group. The polymer is preferably water-soluble.

The polymer may be a homopolymer or a heteropolymer (copolymer), may be modified, may have a known functional group introduced, or may be in the form of a salt. The polymer is preferably a homopolymer.

In the present disclosure, water-solubility of the polymer means that, for example, when 1 g of the polymer is mixed and stirred in 100 g of water having a temperature of 30 degrees C., 90% by mass or greater of the polymer dissolves.

A water-soluble organic polymer is obtained from polymerization of a polymerizable monomer. Examples of the polymerizable monomer include acrylamide, N-substituted acrylamide derivatives, N,N-disubstituted acrylamide derivatives, N-substituted methacrylamide derivatives, and N,N-disubstituted methacrylamide derivatives. One of these polymerizable monomers may be used alone or two or more of these polymerizable monomers may be used in combination.

Through polymerization of the polymerizable monomer, a water-soluble organic polymer containing, for example, an amide group, an amino group, a hydroxyl group, a tetramethylammonium group, a silanol group, or an epoxy group is obtained. A water-soluble organic polymer containing, for example, an amide group, an amino group, a hydroxyl group, a tetramethylammonium group, a silanol group, or an epoxy group is a constituent component advantageous for maintaining the strength of a water-based gel.

The content of the polymerizable monomer is not particularly limited, may be appropriately selected depending on the intended purpose, and is preferably from 0.5% by mass through 20% by mass relative to the total amount of the materials constituting the neutron beam transmission adjusting device.

—Neutron Reactant—

As the neutron reactant contained in the hydrogel, the neutron reactant described above may be used, where appropriate. When a neutron reactant is contained in the mineral, there is no need for separately adding a neutron reactant.

—Organic Solvent—

The organic solvent is used for, for example, enhancing the moisture retaining property of the neutron beam transmission adjusting device of the present disclosure.

Examples of the organic solvent include: alkyl alcohols containing 1 through 4 carbon atoms; amides; ketones or ketone alcohols; ethers; polyalkylene glycols; lower alcohol ethers such as ethylene glycol monomethyl (or ethyl) ether, diethylene glycol methyl (or ethyl) ether, and lower alcohol ethers of polyvalent alcohols; alkanolamines; N-methyl-2-pyrrolidone; 2-pyrrolidone; and 1,3-dimethyl-2-imidazolidinone. Organic solvents described in Japanese Unexamined Patent Application Publication No. 2017-202178 may also be used. One of these organic solvents may be used alone or two or more of these organic solvents may be used in combination. Among these organic solvents, polyvalent alcohols are preferable and glycerin is more preferable in terms of a moisture retaining property.

The addition amount of the organic solvent is preferably 10% by mass or greater but 50% by mass or less relative to the total amount of the materials constituting the neutron beam transmission adjusting device. When the addition amount of the organic solvent is 10% by mass or greater, drying can be effectively suppressed. When the addition amount of the organic solvent is 50% by mass or less, dispersibility of the water-swellable layered clay mineral can be improved.

—Other Components—

The other components are not particularly limited and may be appropriately selected depending on the intended purpose. Examples of the other components include a stabilizing agent, a surface treating agent, a photopolymerization initiator, a colorant, a viscosity modifier, a tackifier, an antioxidant, an age resistor, a cross-linking promoter, an ultraviolet absorber, a plasticizer, an antiseptic, and a dispersant.

For example, the hydrogel precursor is cured using a polymerization initiator, to form a hydrogel. The polymerization initiator described below is used, with the polymerization initiator added in an ink containing the hydrogel precursor.

—Polymerization Initiator—

Examples of the polymerization initiator include a thermal polymerization initiator and a photopolymerization initiator.

The thermal polymerization initiator is not particularly limited and may be appropriately selected depending on the intended purpose. Examples of the thermal polymerization initiator include azo-based initiators, peroxide initiators, persulfate initiators, and redox (oxidoreduction) initiators.

As the photopolymerization initiator, any substance that produces radicals in response to irradiation of light (particularly, an ultraviolet ray having a wavelength of from 220 nm through 400 nm) can be used.

As any of these initiators, initiators described in Japanese Unexamined Patent Application Publication No. 2017-202178 can be used.

<Other Members>

The other members are not particularly limited and may be appropriately selected depending on the intended purpose. Examples of the other members include a supporting member configured to support the neutron beam transmission unit.

A case where the neutron beam transmission adjusting device of the present disclosure is used in the neutron capture therapy has been mainly described so far. Applications of the neutron beam transmission adjusting device are not limited to the neutron capture therapy, but the neutron beam transmission adjusting device may be applied to any applications in which it is desired to modulate neutron beams to desired characteristics.

(Method for Producing Neutron Beam Transmission Adjusting Device)

The method for producing the neutron beam transmission adjusting device of the present disclosure is not particularly limited and may be appropriately selected depending on the intended purpose. Examples of the method include a method using a three-dimensional object producing apparatus (3D printer), a method employing mold formation, and any method known in the art.

As described above, the neutron beam transmission adjusting device of the present disclosure is a device capable of modulating the energy and/or the flux of neutron beams to be transmitted through the device, and is preferably a device configured to optimally modulate neutron beams in accordance with the conditions of a therapy target in consideration of, for example, the lesion site condition (e.g., the seat of disease, the form of the body surface, and a positional relationship with respect to important organs) of the therapy target. Hence, it is preferable that the shape of the neutron beam transmission adjusting device of the present disclosure be determined based on, for example, the lesion site condition data and neutron reaction properties of materials.

The neutron reaction properties (e.g., a neutron attenuating property) of a material constituting the neutron beam transmission adjusting device of the present disclosure can be obtained where appropriate, based on, for example, actual measurement or Monte Carlo calculation. For example, by calculating, for example, the mode of the device, the composition of the materials, and the shape of the device in an optimizing manner based on lesion site shape data of a therapy target, it is possible to generate object formation data for the neutron beam transmission adjusting device. In other words, in the present disclosure, for example, it is preferable to produce the neutron beam transmission adjusting device based on the object formation data corresponding to the lesion site conditions of the irradiation target to be irradiated with neutron beams.

Hence, when producing the neutron beam transmission adjusting device based on object formation data, it is preferable to produce the neutron beam transmission adjusting device using a three-dimensional object producing apparatus, in terms of faithfully (accurately) reproducing the structure represented by the object formation data and improving the shape accuracy.

When forming the neutron beam transmission adjusting device according to the mode of filling a container with a material containing a neutron reactant (mode 1), for example, it is possible to produce the neutron beam transmission adjusting device by producing a container having a hollow structure with a three-dimensional object producing apparatus and filling the container with a liquid or a solid containing a neutron reactant.

When forming the neutron beam transmission adjusting device according to the mode of mixing a neutron reactant with a self-standing material (mode 2), for example, it is possible to produce the neutron beam transmission adjusting device by mixing a neutron reactant in a material (e.g., a hydrogel) that can stand alone after object formation, and performing object forming directly using this material with a three-dimensional object producing apparatus.

In the case of the mode 2, for example, it is also possible to produce the neutron beam transmission adjusting device by pouring a liquid material containing a neutron reactant into a frame having an optional shape (e.g., a container having a hollow structure) in a manner that the frame will have an optional thickness, and subsequently curing the resultant using a curing agent (e.g., a polymerization initiator) to make the material self-standing.

The object forming method of a three-dimensional object producing apparatus that can be used for producing the neutron beam transmission adjusting device is not particularly limited and may be appropriately selected depending on the intended purpose. Examples of the object forming method include inkjet methods including, for example, material jetting methods, stereolithography methods, selective laser sintering methods, and methods of discharging an ink using a dispenser and curing the ink with UV light.

A material jetting method is preferable as the object forming method of a three-dimensional object producing apparatus. When a three-dimensional object producing apparatus is a material jetting type, a device having a desired shape and desired physical properties can be easily formed, with easy controllability of compositional distribution and shape. Moreover, when a three-dimensional object producing apparatus is a material jetting type, a plurality of materials can be used for producing the neutron beam transmission adjusting device, making it possible to form a compositional distribution instead of forming the entire device with the same composition. Particularly, when controlling the neutron reactant concentration distribution in the neutron beam transmission unit in the case of the mode (mode 2) of mixing a neutron reactant in a self-standing material, a material jetting method is preferable because a concentration distribution can be easily formed.

Further, for example, in the case of forming the neutron beam transmission adjusting device according to the mode (mode 1) of filling a container with a substance containing a neutron reactant, it is preferable to form the neutron beam transmission adjusting device, using materials and a method that are free of liquid leakage, in consideration of filling a container with a liquid material.

Furthermore, in the method for producing the neutron beam transmission adjusting device of the present disclosure, it is preferable to control the thickness distribution of the neutron beam transmission unit based on object formation data corresponding to the lesion site condition of an irradiation target to be irradiated with neutron beams. In this way, in the present disclosure, it is possible to appropriately control the energy and/or the flux of neutron beams, improve the therapeutic effect of the neutron capture therapy, and suppress neutron beams to be irradiated to normal tissues surrounding the lesion site.

In the method for producing the neutron beam transmission adjusting device of the present disclosure, it is preferable to control the neutron reactant concentration distribution based on object formation data corresponding to the lesion site condition of an irradiation target to be irradiated with neutron beams. In this way, in the present disclosure, it is possible to appropriately control the energy and/or the flux of neutron beams, improve the therapeutic effect of the neutron capture therapy, and suppress neutron beams to be irradiated to normal tissues surrounding the lesion site.

Figure 3:
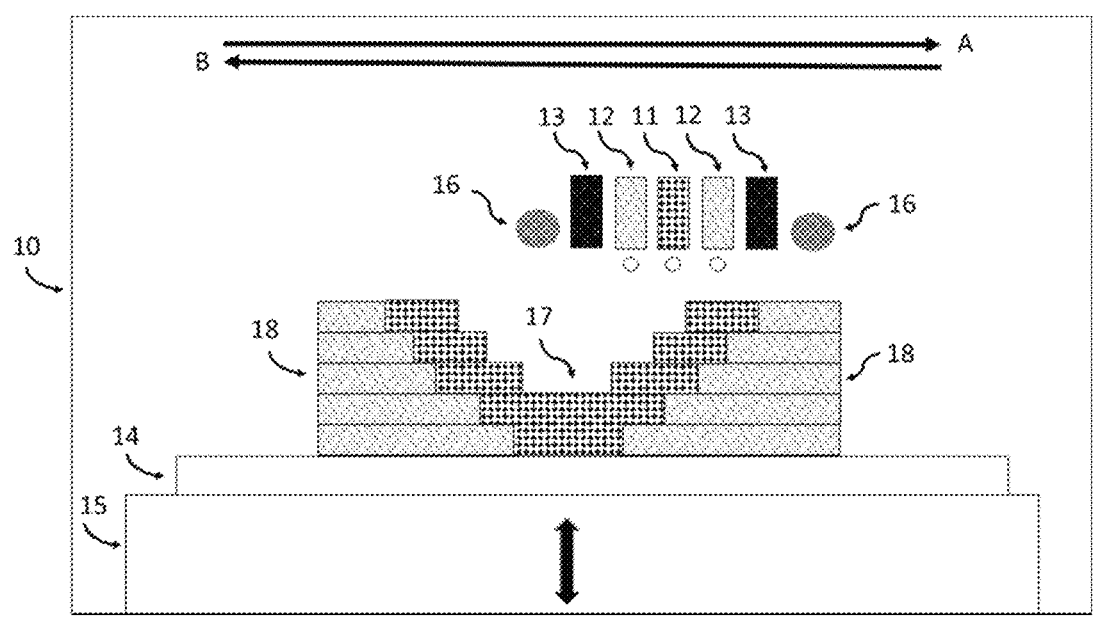
FIG. 3 is a view illustrating an example of how a neutron beam transmission adjusting device is produced using a material jetting-type three-dimensional object producing apparatus.

FIG. 3 is a view illustrating an example of how the neutron beam transmission adjusting device is produced using a material jetting-type three-dimensional object producing apparatus.

A material jetting (MJ)-type 3D (three-dimensional) printer 10 illustrated in FIG. 3 is configured to use head units in which inkjet heads are arrayed, and laminate layers by discharging a liquid material for forming a device from a head unit 11 for discharging the liquid material for forming a device and a liquid material for forming a support from head units 12 for discharging the liquid material for forming a support toward an object support substrate 14 while curing the liquid material for forming a device and the liquid material for forming a support with adjoining ultraviolet irradiators 13.

For example, it is preferable to use a hydrogel precursor liquid as the liquid material for forming a device. The liquid material for forming a support is not particularly limited and may be appropriately selected depending on the intended purpose so long as the liquid material for forming a support can be discharged from an inkjet head and can be cured with energy rays such as ultraviolet rays. Examples of the liquid material for forming a support include acrylic-based materials.

In order to maintain the head units 11 and 12 for discharging the liquid materials and the ultraviolet irradiators 13 at a constant gap from the object (device) 17 and the support (support material) 18, layers are laminated while lifting down the stage 15 in accordance with the number of times layers are laminated.

In the three-dimensional printer 10, the ultraviolet irradiators 13 are used in moving in both of the directions of arrows A and B, and the surfaces of the laminated layers of the liquid material for forming a support are smoothed by heat generated from ultraviolet irradiation. As a result, the dimensional stability of the object (device) 17 can be improved.

Figure 4:
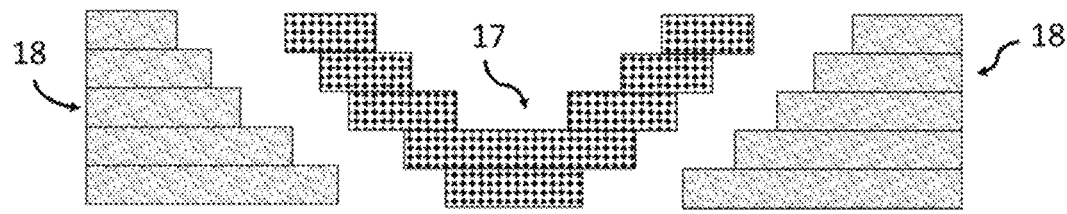
FIG. 4 is a view illustrating an example of how a support is detached from a neutron beam transmission adjusting device formed using a material jetting-type three-dimensional object producing apparatus.

After object formation is completed, the device 17 and the support 18 are pulled in the horizontal direction as illustrated in FIG. 4. As a result, the support 18 is detached as integrated bodies, and the device 17 can be easily taken out.

The three-dimensional printer 10 may additionally include a mechanism configured to recover and recycle the materials for forming, a blade configured to remove the materials for forming adhering to nozzle surfaces, and a detection mechanism configured to detect non-discharging nozzles. It is also preferable that the three-dimensional printer 10 be configured to control the environmental temperature in the apparatus during object formation. It is preferable that the three-dimensional printer 10 include a smoothing member 16 configured to smooth the liquid material for forming a device discharged.

Examples of the method for controlling the neutron reactant concentration distribution include adjusting the amount of the solvent to be contained in the liquid material for forming a device (e.g., a hydrogel precursor liquid). For example, this can be realized using an apparatus that can hold a plurality of liquid materials for forming a device having different neutron reactant concentrations and that includes a unit configured to discharge these liquid materials for forming a device from respective inkjet heads.

Moreover, the method for controlling the neutron reactant concentration distribution may be a mode of, for example, discharging a liquid material for forming a device having a predetermined neutron reactant concentration and a liquid for concentration adjustment (e.g., pure water) from respective inkjet heads. In this case, for example, it is possible to control the neutron reactant concentration distribution by controlling the ratio by weight between the liquid material for forming a device and the liquid for concentration adjustment over an object formation plane. Moreover, it may be possible to control the neutron reactant concentration distribution by controlling the discharging amount of the liquid material for forming a device to be discharged from an inkjet head.

Using the apparatus described above, it is possible to easily control the thickness of neutron beam transmission unit and the neutron reactant concentration distribution in the neutron beam transmission adjusting device in accordance with object formation data corresponding to the lesion site condition of an irradiation target to be irradiated with neutron beams, making it possible to appropriately control the energy and/or the flux of neutron beams to be transmitted through the neutron beam transmission adjusting device.

<Neutron Beam Adjusting Method (Cancer Treating Method)>

The neutron beam transmission adjusting device of the present disclosure can be suitably used in a neutron beam adjusting method of the present disclosure. The neutron beam adjusting method of the present disclosure can be appropriately used depending on the intended purpose, when adjusting the neutron beam to be irradiated. For example, the neutron beam adjusting method is suitably used in the neutron capture therapy. The irradiation target in the neutron beam adjusting method is not particularly limited and may be appropriately selected depending on the intended purpose. The irradiation target is not particularly limited to a patient of the neutron capture therapy.

For example, it is possible to effectively kill cancer cells, by, as described above, disposing the neutron beam transmission adjusting device of the present disclosure between a collimator and a patient body as illustrated in FIG. 2B and FIG. 2C and irradiate each target region with neutron beams optimally modulated for the target. This makes it possible to not only enhance the therapeutic effect but also reduce the side effects on the surrounding healthy tissue. Hence, the neutron capture therapy using the neutron beam transmission adjusting device of the present disclosure is a groundbreaking cancer treating method (cancer treatment). Hence, the neutron beam adjusting method (cancer treating method) of the present disclosure can be suitably applied to the neutron capture therapy.

For example, the neutron beam adjusting method (cancer treating method) of the present disclosure includes the following steps of:

(a) irradiating a therapy target with neutron beams through a neutron beam transmission adjusting device.

As the neutron beam transmission adjusting device used in the neutron beam adjusting method (cancer treating method) of the present disclosure, the neutron beam transmission adjusting device described above can be used. As described above, the neutron beam transmission adjusting device may be disposed, for example, between a neutron beam source and an irradiation target (patient) on the neutron beam path, and may be disposed at an immediately succeeding position of a collimator (at the irradiation target side), or at a position on the body surface of a patient, who is the therapy target. In other words, in the neutron beam adjusting method (cancer treating method) of the present disclosure, for example, when irradiating an irradiation target of neutron beams from a neutron beam source with neutron beams, the neutron beam transmission adjusting device of the present disclosure is disposed between the source and the irradiation target on the neutron beam path. In the neutron beam adjusting method (cancer treating method) of the present disclosure, it is preferable to perform modulation in accordance with the conditions of the irradiation target, using the neutron beam transmission adjusting device of the present disclosure.

In a preferable mode, the neutron beam adjusting method (cancer treating method) of the present disclosure may further include at least any one selected from the following steps before the step (a):

(a-1) obtaining lesion site condition data of a treatment target (therapy target); and (a-2) producing a neutron beam transmission adjusting device.

The step (a-1) is a step of obtaining lesion site condition data of the treatment target. As described above, the lesion site condition data can be obtained based on all kinds of medical data relating to the disease of the treatment target, such as CT data, MRI data, and roentgenography data.

The step (a-2) is a step of producing a neutron beam transmission adjusting device. A versatile device configured to modulate neutron beams to a predetermined energy or a predetermined flux, or both may be produced, or an exclusive device for the treatment target, capable of performing modulation optimized for the treatment target (i.e., modulation in accordance with the lesion site conditions of the treatment target) may be produced. In this case, for example, the lesion site condition data used for generating object formation data for producing the exclusive device for the treatment target may be data obtained in the step (a-1) or may be any other data.

In the step (a-2), for example, the method for producing the neutron beam transmission adjusting device of the present disclosure described above may be used.

The steps (a-1) and (a-2) may be included in the neutron beam adjusting method (cancer treating method) independently from each other. The order of these steps may be appropriately selected. However, both of these steps are performed before the step (a).

EXAMPLES

The present disclosure will be more specifically described below by way of Examples. The present disclosure should not be construed as being limited to these Examples.

Example 1

In Example 1, a neutron beam transmission adjusting device formed of a hydrogel and entirely formed of a neutron beam transmission unit was produced as an example of the neutron beam transmission adjusting device of the present disclosure.

<Preparation of Hydrogel Forming Material 1>

First, to pure water (1,060 parts by mass) under stirring, a neutron reactant-containing mineral, which was synthetic hectorite having the composition of $[Mg_{5.34}Li_{0.66}Si_8O_{20}(OH)_4]Na_{0.66}$ (LAPONITE XLG, obtained from Rock Wood) (60 parts by mass) was added little by little, and 1-hydroxyethane-1,1-diphosphonic acid (3 parts by mass) was further added. The resultant was stirred, to prepare a dispersion liquid.

Next, to the obtained dispersion liquid, polymerizable monomers, which were N,N-dimethylacrylamide passed through an activated alumina column for removal of a polymerization inhibitor (obtained from FUJIFILM Wako Pure Chemical Corporation) (30 parts by mass), acryloylmorpholine (obtained from Tokyo Chemical Industry Co., Ltd.) (180 parts by mass), and methylenebisacrylamide (obtained from Tokyo Chemical Industry Co., Ltd.) (2.5 parts by mass), and glycerin (obtained from Tokyo Chemical Industry Co., Ltd.) (120 parts by mass) were added. Subsequently, to the resultant under cooling in an ice bath, tetramethylethylenediamine (obtained from FUJIFILM Wako Pure Chemical Corporation) (4 parts by mass) was added, stirred and mixed, and degassed at reduced pressure for 10 minutes. Next, the resultant was filtrated to remove, for example, impurities, to obtain a homogeneous hydrogel forming material 1.

<Production of Neutron Beam Transmission Adjusting Device 1>

To the produced hydrogel forming material 1 (100 parts by weight), a 2% by weight aqueous solution (8.4 parts by weight) of potassium peroxodisulfate (obtained from FUJI-FILM Wako Pure Chemical Corporation) was added as a polymerization initiator. The resultant was poured into a container having a size of 10 cm in depth, 10 cm in width, and 4 cm in height in a manner that the average thickness of a neutron beam transmission adjusting device would be 3 mm, and tightly sealed, to produce a neutron beam transmission adjusting device 1.

Example 2

A neutron beam transmission adjusting device 2 was produced in the same manner as in Example 1, except that unlike in Example 1, the average thickness of the neutron beam transmission adjusting device was set to 5 mm.

Example 3

A neutron beam transmission adjusting device 3 was produced in the same manner as in Example 1, except that unlike in Example 1, the average thickness of the neutron beam transmission adjusting device was set to 10 mm.

Example 4

A neutron beam transmission adjusting device 4 was produced in the same manner as in Example 1, except that unlike in Example 1, the average thickness of the neutron beam transmission adjusting device was set to 20 mm.

Example 5

A neutron beam transmission adjusting device 5 was produced in the same manner as in Example 1, except that unlike in Example 1, the average thickness of the neutron beam transmission adjusting device was set to 35 mm.

Figure 6:
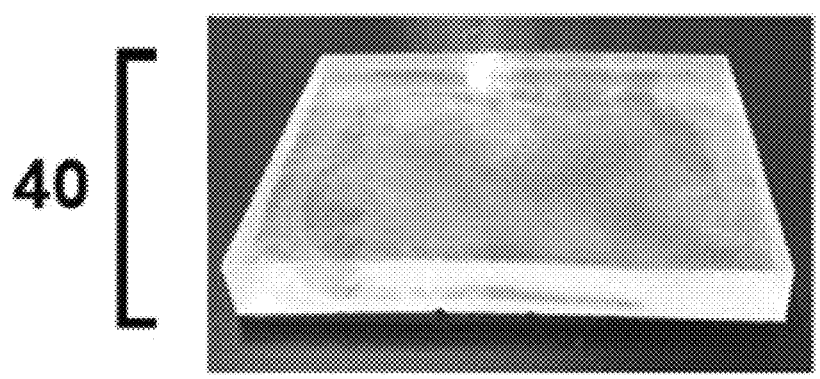
FIG. 6 is an image captured of a neutron beam transmission adjusting device of Example 3.

FIG. 6 is an image captured of the neutron beam transmission adjusting device of Example 3. It can be seen from FIG. 6 that a neutron beam transmission adjusting device formed of a hydrogel and entirely formed of a neutron beam transmission unit 40 was successfully produced.

<Evaluation of Attenuating Characteristic of Neutron Beams and Thickness>

Using the neutron beam transmission adjusting devices 1 to 5, the attenuating characteristics of neutron beams transmitted through the neutron beam transmission adjusting devices were measured.

Using a neutron beam irradiating device, neutron beams were irradiated in the direction of the thickness of the neutron beam transmission adjusting devices, and relative intensities of the neutron fluxes of the irradiated neutron beams measured at the surface (entrance) exposed to the neutron beams and at the surface (exit) through which the transmitted neutron beams would exit were compared with each other.

Figure 7:
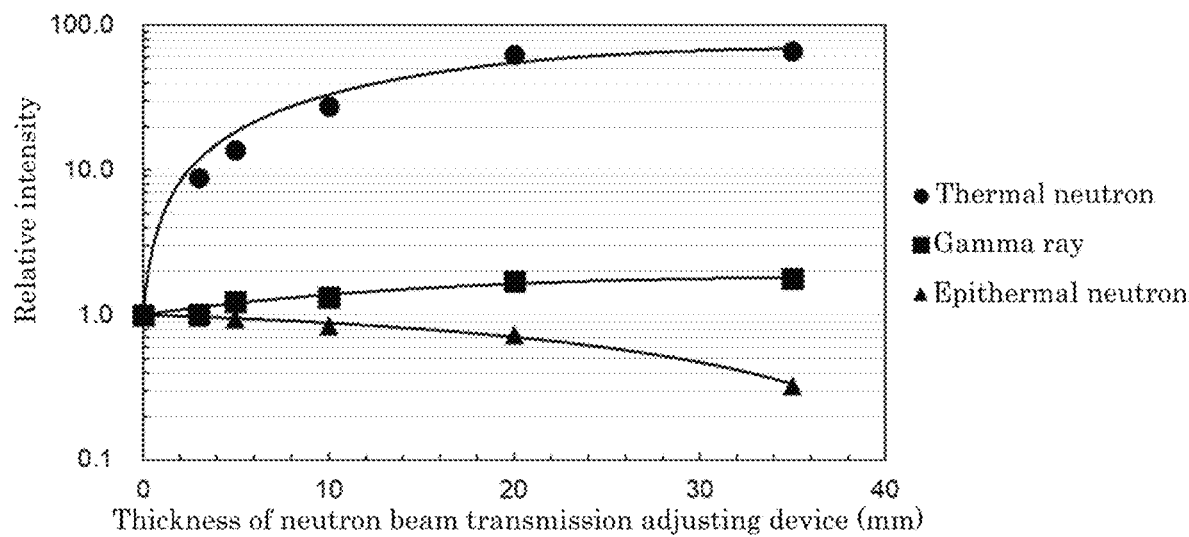
FIG. 7 is a graph plotting an example dependency of neutron beams transmitted through neutron beam transmission adjusting devices on thickness of a neutron reactant.

FIG. 7 is a graph plotting an example dependency of the neutron beams transmitted through the neutron beam transmission adjusting devices on the thickness of the neutron reactant. In FIG. 7, the vertical axis represents relative intensity expressing an intensity at the exit surface when there was a neutron beam transmission adjusting device, relative to an intensity at a corresponding plane when there was no neutron beam transmission adjusting device, and the horizontal axis represents the average thickness of the neutron beam transmission adjusting devices. It can be seen from FIG. 7 that the neutron beam transmission adjusting device of the present disclosure was able to modulate the energy and/or the flux of neutron beams transmitted through the neutron beam transmission adjusting device, judging from that the relative intensities of the neutron fluxes varied depending on the thickness of the neutron beam transmission adjusting devices and that the ratios between thermal neutron and epithermal neutron varied depending on the thickness of the neutron beam transmission adjusting devices.

Example 6

<Preparation of Hydrogel Forming Material 2>

To pure water (700 parts by mass) under stirring, a neutron reactant-containing mineral, which was synthetic hectorite having the composition of $[Mg_{5.34}Li_{0.66}Si_8O_{20}(OH)_4]Na_{0.66}$ (LAPONITE XLG, obtained from Rock Wood) (60 parts by mass) was added little by little, and 1-hydroxyethane-1,1-diphosphonic acid (3 parts by mass) was further added. The resultant was stirred, to prepare a dispersion liquid.

Next, to the obtained dispersion liquid, polymerizable monomers, which were N,N-dimethylacrylamide passed through an activated alumina column for removal of a polymerization inhibitor (obtained from FUJIFILM Wako Pure Chemical Corporation) (30 parts by mass), acryloylmorpholine (obtained from Tokyo Chemical Industry Co., Ltd.) (180 parts by mass), and methylenebisacrylamide (obtained from Tokyo Chemical Industry Co., Ltd.) (2.5 parts by mass), and glycerin (obtained from Tokyo Chemical Industry Co., Ltd.) (120 parts by mass) were added. Subsequently, to the resultant under cooling in an ice bath, tetramethylethylenediamine (obtained from FUJIFILM Wako Pure Chemical Corporation) (4 parts by mass) was added, stirred and mixed, and degassed at reduced pressure for 10 minutes. Next, the resultant was filtrated to remove, for example, impurities, to obtain a homogeneous hydrogel forming material 2.

In other words, the hydrogel forming material 2 was prepared in the same manner as in Preparation of hydrogel forming material 1, except that unlike in Preparation of hydrogel forming material 1, the amount of the pure water was changed to 700 parts by mass.

<Preparation of Material for Forming Support>

Dodecyl acrylate (obtained from Tokyo Chemical Industry Co., Ltd.) (29 parts by mass), stearyl acrylate (obtained from Tokyo Chemical Industry Co., Ltd.) (29 parts by mass), 1-hydroxycyclohexylphenyl ketone (obtained from BASF Japan Ltd., product name: IRGACURE 184) (2 parts by mass), and 1-dodecanol (obtained from Tokyo Chemical Industry Co., Ltd.) (40 parts by mass) were stirred until a homogeneous mixture was obtained. Subsequently, the resultant was filtrated to remove, for example, impurities, and further degassed in vacuum for 10 minutes, to obtain a homogeneous material for forming a support.

<Production of Neutron Beam Transmission Adjusting Device 6>

Four inkjet heads (obtained from Ricoh Industry Co., Ltd., GEN 4) of a material jetting-type three-dimensional printer illustrated in FIG. 3 were filled with the hydrogel forming material 2, pure water for concentration adjustment, and the material for forming a support.

In production of a neutron beam transmission adjusting device 6, object formation (film formation) was performed in a manner that the hydrogel forming material 2 and the pure water for concentration adjustment would be at a ratio by weight of 100:0 over the object formation plane (discharge plane).

Then, using an ultraviolet irradiator (obtained from Ushio Inc., SPOT CURE SP5-250DB), the hydrogel forming material 2 and the material for forming a support were cured with irradiation of a light volume of 350 mJ/cm$^2$, to form a cured product of the hydrogel forming material 2 and a support. The support was formed in a manner to surround the contour of the cured product of the hydrogel forming material 2.

After object formation, the cured product of the hydrogel forming material 2 and the support were detached from each other, to produce a neutron beam transmission adjusting device 6 formed of the cured product of the hydrogel forming material 2.

In this way, the neutron beam transmission adjusting device 6 having a similar shape to the neutron beam transmission adjusting device 1 produced in Example 1 was produced with the three-dimensional printer mentioned above. The neutron beam transmission adjusting device 6 was produced to have a size of 10 cm in depth, 10 cm in width, and 10 mm in thickness.

Example 7

A neutron beam transmission adjusting device 7 was produced in the same manner as in Example 6, except that unlike in Example 6, object formation was performed in a manner that the hydrogel forming material 2 and the pure water for concentration adjustment would be at a ratio by weight of 90:10 over the object formation plane (discharge plane).

Example 8

A neutron beam transmission adjusting device 8 was produced in the same manner as in Example 6, except that unlike in Example 6, object formation was performed in a manner that the hydrogel forming material 2 and the pure water for concentration adjustment would be at a ratio by weight of 75:25 over the object formation plane (discharge plane).

Example 9

A neutron beam transmission adjusting device 9 was produced in the same manner as in Example 6, except that unlike in Example 6, object formation was performed in a manner that the hydrogel forming material 2 and the pure water for concentration adjustment would be at a ratio by weight of 50:50 over the object formation plane (discharge plane).

<Evaluation of Attenuating Characteristic of Neutron Beams and Neutron Reactant Concentration>

Using the neutron beam transmission adjusting devices 6 to 9, the attenuating characteristics of neutron beams transmitted through the neutron beam transmission adjusting devices were measured.

Using a neutron beam irradiating device, neutron beams were irradiated in the direction of the thickness of the neutron beam transmission adjusting devices, and relative intensities of the neutron fluxes of the irradiated neutron beams measured at the surface (entrance) exposed to the neutron beams and at the surface (exit) through which the transmitted neutron beams would exit were compared with each other.

Figure 8:
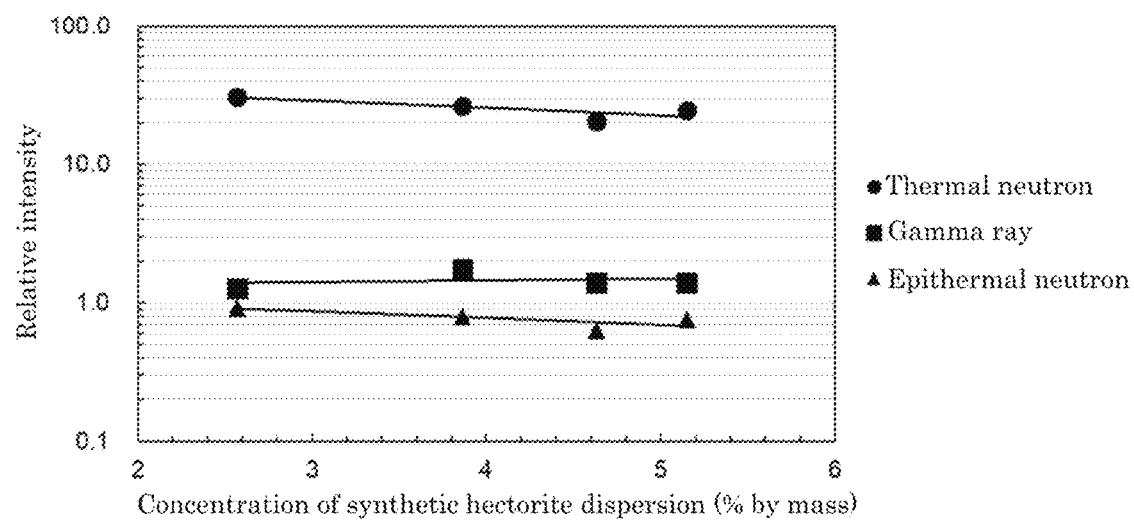
FIG. 8 is a graph plotting an example dependency of neutron beams transmitted through neutron beam transmission adjusting devices on concentration of a neutron reactant.

FIG. 8 is a graph plotting an example dependency of the neutron beams transmitted through the neutron beam transmission adjusting devices on the concentration of the neutron reactant. In FIG. 8, the vertical axis represents relative intensity expressing an intensity at the exit surface when there was a neutron beam transmission adjusting device, relative to an intensity at a corresponding plane when there was no neutron beam transmission adjusting device, and the horizontal axis represents the concentration (% by mass) of the synthetic hectorite dispersion containing the neutron reactant. The plots in FIG. 8 are plots of the results of Examples 9, 8, 7, and 6 from left to right. It can be seen from FIG. 8 that the neutron beam transmission adjusting device of the present disclosure was able to modulate the energy and/or the flux of neutron beams transmitted through the neutron beam transmission adjusting device, judging from that the relative intensities of the neutron fluxes varied depending on the concentration of the neutron reactant and that the ratios between thermal neutron and epithermal neutron varied depending on the concentration of the neutron reactant.

Next, Examples of the neutron beam transmission adjusting device of the present disclosure in the case of installing the neutron beam transmission adjusting device on the collimator of a neutron beam irradiating device and performing modulation in accordance with the lesion site conditions of an irradiation target will be described.

Neutron attenuating properties of the hydrogel forming material used in Examples 10 to 15 below (neutron attenuating properties: e.g., changes of the energy spectrum, the neutron flux, and the γ-ray dose rate of neutrons when transmitted through the neutron beam transmission adjusting device) were measured beforehand, to enable modulation in accordance with the lesion site conditions of the irradiation target (patient).

Object formation data used in these Examples were generated in accordance with the lesion site conditions of the patient to be irradiated with neutron beams, based on the results of calculation of the neutron reaction properties of the materials constituting the neutron beam transmission adjusting device, obtained from actual measurement and simulation (Monte Carlo calculation).

Example 10

Four inkjet heads (obtained from Ricoh Industry Co., Ltd., GEN 4) of a material jetting-type three-dimensional printer illustrated in FIG. 3 were filled with the hydrogel forming material 1 and the material for forming a support.

In production of a neutron beam transmission adjusting device, object formation was performed based on object formation data generated in accordance with the neutron attenuating properties of the hydrogel forming material 1 based on CT data of the lesion site as illustrated in FIG. 1.

Then, using an ultraviolet irradiator (obtained from Ushio Inc., SPOT CURE SP5-250DB), the hydrogel forming material 1 and the material for forming a support were cured with irradiation of a light volume of 350 mJ/cm$^2$, to form a cured product of the hydrogel forming material 1 and a support.

After object formation, the cured product of the hydrogel forming material 1 and the support were detached from each other, to produce a neutron beam transmission adjusting device 30 turned of the cured product of the hydrogel forming material 1.

Example 11

<Preparation of Hydrogel Forming Material 3>

To pure water (700 parts by mass) under stirring, a neutron reactant-containing mineral, which was synthetic hectorite having the composition of $[Mg_{5.34}Li_{0.66}Si_8O_{20}(OH)_4]Na_{0.66}$ (LAPONITE XLG, obtained from Rock Wood) (6 parts by mass) was added little by little, and 1-hydroxyethane-1,1-diphosphonic acid (3 parts by mass) was further added. The resultant was stirred, to prepare a dispersion liquid.

Next, to the obtained dispersion liquid, polymerizable monomers, which were N,N-dimethylacrylamide passed through an activated alumina column for removal of a polymerization inhibitor (obtained from FUJIFILM Wako Pure Chemical Corporation) (30 parts by mass), acryloylmorpholine (obtained from Tokyo Chemical Industry Co., Ltd.) (180 parts by mass), and methylenebisacrylamide (obtained from Tokyo Chemical Industry Co., Ltd.) (2.5 parts by mass), and glycerin (obtained from Tokyo Chemical Industry Co., Ltd.) (120 parts by mass) were added.

Subsequently, to the resultant under cooling in an ice bath, tetramethylethylenediamine (obtained from FUJIFILM Wako Pure Chemical Corporation) (4 parts by mass) was added, stirred and mixed, and degassed at reduced pressure for 10 minutes. Next, the resultant was filtrated to remove, for example, impurities, to obtain a homogeneous hydrogel forming material 3.

In other words, the hydrogel forming material 3 was prepared in the same manner as in Preparation of hydrogel forming material 2, except that unlike in Preparation of hydrogel forming material 2, the amount of the synthetic hectorite was changed to 6 parts by mass. Hence, the concentration of the synthetic hectorite (Li atom concentration) was about 1/10 of the concentration in the hydrogel forming material 2.

<Production of Neutron Beam Transmission Adjusting Device 11>

Four inkjet heads (obtained from Ricoh Industry Co., Ltd., GEN 4) of a material jetting-type three-dimensional printer illustrated in FIG. 3 were filled with the hydrogel forming material 2, the hydrogel forming material 3, and the material for forming a support. The hydrogel forming material 2 and the hydrogel forming material 3 were discharged from different inkjet heads, and mixed over the object formation plane at a ratio that was based on object formation data generated in accordance with the neutron attenuating properties of the hydrogel forming materials 2 and 3 based on CT data of the lesion site as illustrated in FIG. 1, to control the distribution of the concentration of the neutron reactant (Li atom) and form a Li atom concentration distribution.

Then, using an ultraviolet irradiator (obtained from Ushio Inc., SPOT CURE SP5-250DB), the hydrogel forming materials 2 and 3 and the material for forming a support were cured with irradiation of a light volume of 350 mJ/cm$^2$, to form cured products of the hydrogel forming materials 2 and 3 and a support.

After object formation, the cured products of the hydrogel forming materials 2 and 3 were detached from the support, to produce a neutron beam transmission adjusting device 11 formed of the cured products of the hydrogel forming materials 2 and 3.

Example 12

In Example 12, a neutron beam transmission adjusting device according to the mode of filling a container formed of a hard shaped body with a material containing a neutron reactant was produced as an example of the neutron beam transmission adjusting device of the present disclosure.

<Preparation of Neutron Reactant-Containing Liquid 1>

Boron was selected as the neutron reactant. Specifically, sodium metaborate tetrahydrate (obtained from FUJIFILM Wako Pure Chemical Corporation) (5 parts by mass) and pure water (95 parts by mass) were mixed, to prepare a neutron reactant-containing liquid 1.

<Preparation of Material for Hard Shaped Body>

A curable material 1, which was urethane acrylate (obtained from Mitsubishi Rayon Co., Ltd., product name: DIABEAM UK6038) (10 parts by mass), a curable material 2, which was neopentyl glycol hydroxypivalic acid ester di(meth)acrylate (obtained from Nippon Kayaku Co., Ltd., product name: KAYARAD MANDA) (90 parts by mass), and a photopolymerization initiator (obtained from BASF Japan Ltd., product name: IRGACURE 184) (3 parts by mass) were stirred until a homogeneous mixture was obtained. Subsequently, the resultant was filtrated to remove, for example, impurities, and further degassed in vacuum for 10 minutes, to obtain a homogeneous material for a hard shaped body.

<Formation of Container>

Four inkjet heads (obtained from Ricoh Industry Co., Ltd., GEN 4) of a material jetting-type three-dimensional printer illustrated in FIG. 3 were filled with the material for a hard shaped body and the material for forming a support.

In production of a neutron beam transmission adjusting device, object formation was performed based on object formation data generated in accordance with the neutron attenuating property of the neutron reactant-containing liquid 1 based on CT data of the lesion site as illustrated in FIG. 1.

Then, using an ultraviolet irradiator (obtained from Ushio Inc., SPOT CURE SP5-250DB), the material for a hard shaped body and the material for forming a support were cured with irradiation of a light volume of 350 mJ/cm$^2$, to form a container and a support.

After object formation, the container and the support were detached from each other (the support inside the container was heated and taken out in a liquid state), to produce a container having a hollow shape and a container frame thickness of 1 mm.

<Production of Neutron Beam Transmission Adjusting Device 12>

The produced container was filled with the neutron reactant-containing liquid 1, to produce a neutron beam transmission adjusting device 12.

Example 13

<Preparation of Neutron Reactant-Containing Liquid 2>

Lithium was selected as the neutron reactant. Specifically, trilithium citrate tetrahydrate (obtained from FUJIFILM Wako Pure Chemical Corporation) (5 parts by mass) and pure water (95 parts by mass) were mixed, to prepare a neutron reactant-containing liquid 2.

A neutron beam transmission adjusting device 13 was produced in the same manner as in Example 12, except that unlike in Example 12, object formation data in accordance with the neutron attenuating property of the neutron reactant-containing liquid 2 was used.

Example 14

<Preparation of Neutron Reactant-Containing Liquid 3>
Gadolinium was selected as the neutron reactant. Specifically, gadolinium chloride hexahydrate (obtained from FUJIFILM Wako Pure Chemical Corporation) (5 parts by mass) and pure water (95 parts by mass) were mixed, to prepare a neutron reactant-containing liquid 3.
A neutron beam transmission adjusting device 14 was produced in the same manner as in Example 12, except that unlike in Example 12, object formation data in accordance with the neutron attenuating property of the neutron reactant-containing liquid 3 was used.

Example 15

In Example 15, a neutron beam transmission adjusting device having a shape conforming to the body surface of a patient was produced as an example of the neutron beam transmission adjusting device of the present disclosure.
Specifically, a neutron beam transmission adjusting device 30 was produced in the same manner as in Example 10, except that unlike in Example 10, body surface profile (surface bump or dent) data of a neutron beam irradiation part of the patient was obtained, to use object formation data for shaping one side of the neutron beam transmission adjusting device in a manner to fit the body surface.
Evaluation of these Examples may be performed by, for example, disposing the neutron beam transmission adjusting device between a collimator and a patient as illustrated in FIG. 2B, measuring the distribution of the neutron flux near the lesion site, and comparing the measured distribution with an optimum neutron flux distribution obtained based on the form of the seat of disease identified from, for example, CT data of the patient.
Production examples of neutron beam transmission adjusting devices having other shapes will be described below.
In Examples 16 to 18 below, neutron beam transmission adjusting devices 16 to 18 having a structure formed of stacked, integrated two circular columns having different diameters from each other were produced in the same manner as in Example 6.

Example 16

In Example 16, a neutron beam transmission adjusting device 16 was produced in the same manner as in Example 6, except that unlike in Example 6, object formation data for forming a circular columnar part having a diameter of 10 cm and a thickness of 10 mm as the lower stage (lower layer) and forming a circular columnar part having a diameter of 6 cm and a thickness of 10 mm as the upper stage (upper layer) to obtain a total thickness of 20 mm was used for a neutron beam transmission adjusting device having a structure formed of stacked two circular columns having different diameters from each other.

Example 17

In Example 17, a neutron beam transmission adjusting device 17 was produced in the same manner as in Example 16, except that unlike in Example 16, object formation data for forming a circular columnar part constituting the lower stage and a circular columnar part constituting the upper stage to have a thickness of 5 mm each to obtain a total thickness of 10 mm was used.

Example 18

Figure 9:
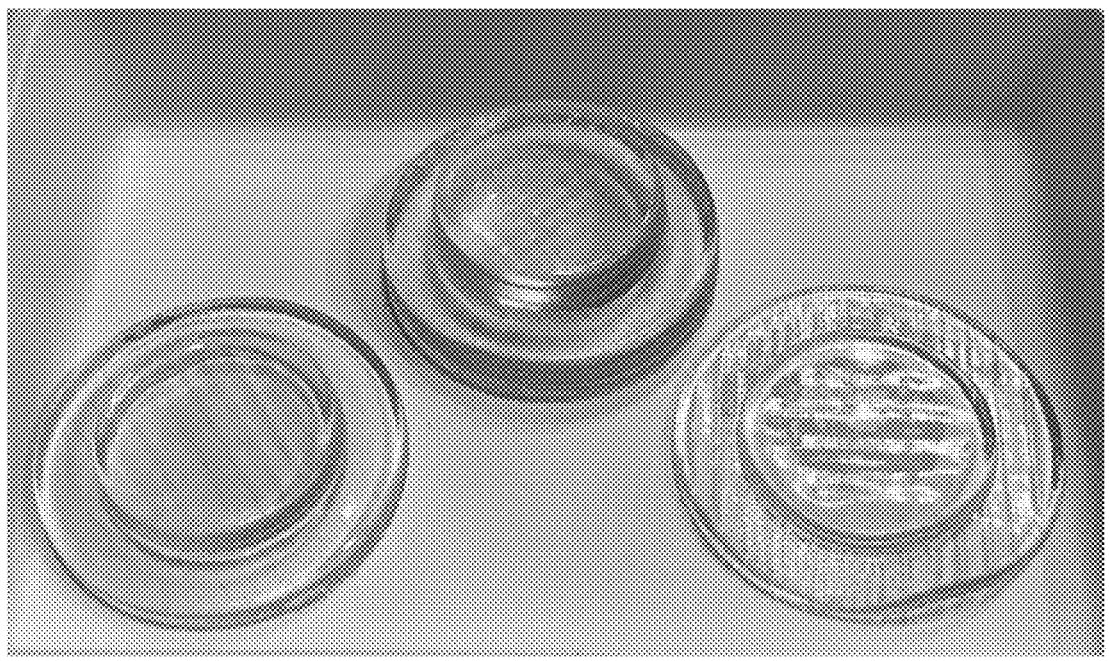
FIG. 9 is a captured image of neutron beam transmission adjusting devices of Examples 16 to 18.

In Example 18, a neutron beam transmission adjusting device 18 was produced in the same manner as in Example 16, except that unlike in Example 16, object formation data for forming a circular columnar part constituting the lower stage and a circular columnar part constituting the upper stage to have a thickness of 2.5 mm each to obtain a total thickness of 5 mm was used.
FIG. 9 is a captured image of the neutron beam transmission adjusting devices of Examples 16 to 18.
In FIG. 9, the neutron beam transmission adjusting device 16 of Example 16 (with a thickness of 20 mm) is illustrated at the center, the neutron beam transmission adjusting device 17 of Example 17 (with a thickness of 10 mm) is illustrated at the left, and the neutron beam transmission adjusting device 18 of Example 18 (with a thickness of 5 mm) is illustrated at the right.
As illustrated in FIG. 9, in any of Examples 16 to 18, a neutron beam transmission adjusting device having the desired shape was successfully produced according to the object formation data.
As described above, the neutron beam transmission adjusting device of the present disclosure includes a neutron beam transmission unit including a neutron reactant and capable of modulating the energy and/or the flux of neutron beams transmitted through the neutron beam transmission unit. Hence, the neutron beam transmission adjusting device of the present disclosure can have the neutron beams that have been transmitted through the neutron beam transmission unit modulated to desired characteristics.
Aspects of the present disclosure are, for example, as follows.
<1> A neutron beam transmission adjusting device including
a neutron beam transmission unit including a neutron reactant and capable of modulating at least any one selected from the group consisting of an energy and a flux of a neutron beam transmitted through the neutron beam transmission unit.
<2> The neutron beam transmission adjusting device according to <1>,
wherein the neutron beam transmission adjusting device is used in a neutron capture therapy.
<3> The neutron beam transmission adjusting device according to <2>,
wherein the neutron beam transmission adjusting device is used, with the neutron beam transmission adjusting device disposed between a source of the neutron beam and an irradiation target to be irradiated with the neutron beam on a path of the neutron beam, and
wherein the neutron beam transmission unit is configured to perform modulation in accordance with a lesion site condition of the irradiation target.
<4> The neutron beam transmission adjusting device according to any one of <1> to <3>,
wherein the neutron reactant contains at least any one selected from the group consisting of a boron atom, a lithium atom, and a gadolinium atom.

<5> The neutron beam transmission adjusting device according to any one of <1> to <4>,
wherein the neutron beam transmission unit has a thickness distribution.
<6> The neutron beam transmission adjusting device according to any one of <1> to <5>,
wherein the neutron beam transmission unit has a concentration distribution of the neutron reactant.
<7> The neutron beam transmission adjusting device according to any one of <1> to <6>,
wherein the neutron beam transmission unit is deformable.
<8> The neutron beam transmission adjusting device according to <3>,
wherein the neutron beam transmission unit has a shape conforming to a surface of the irradiation target.
<9> The neutron beam transmission adjusting device according to any one of <1> to <8>,
wherein the neutron beam transmission unit contains a hydrogel containing water, a polymer, and a mineral.
<10> A method for producing a neutron beam transmission adjusting device, the method including
producing the neutron beam transmission adjusting device according to any one of <1> to <9> using a three-dimensional object producing apparatus.
<11> The method for producing a neutron beam transmission adjusting device according to <10>,
wherein the three-dimensional object producing apparatus is a material jetting type.
<12> The method for producing a neutron beam transmission adjusting device according to <10> or <11>,
wherein the neutron beam transmission adjusting device is produced based on object formation data corresponding to a lesion site condition of an irradiation target to be irradiated with the neutron beam.
<13> The method for producing a neutron beam transmission adjusting device according to <12>,
wherein a thickness distribution of the neutron beam transmission unit is controlled based on the object formation data.
<14> The method for producing a neutron beam transmission adjusting device according to <12> or <13>,
wherein a concentration distribution of the neutron reactant in the neutron beam transmission unit is controlled based on the object formation data.
<15> A neutron beam adjusting method including
when irradiating an irradiation target of a neutron beam from a source of the neutron beam with the neutron beam, disposing the neutron beam transmission adjusting device according to any one of <1> to <9> between the source and the irradiation target on a path of the neutron beam.
<16> The neutron beam adjusting method according to <15>, including
performing modulation with the neutron beam transmission adjusting device in accordance with a condition of the irradiation target.
<17> A cancer treating method including
using the neutron beam transmission adjusting device according to any one of <1> to <9>.
<18> The cancer treating method according to <17>, including
when irradiating an irradiation target of the neutron beam from a source of the neutron beam with the neutron beam, disposing the neutron beam transmission adjusting device between the source and the irradiation target on a path of the neutron beam.
<19> The cancer treating method according to <17> or <18>, including
performing modulation using the neutron beam transmission adjusting device in accordance with a lesion site condition of the irradiation target.

The neutron beam transmission adjusting device according to any one of <1> to <9>, the method for producing a neutron beam transmission adjusting device according to any one of <10> to <14>, the neutron beam adjusting method according to <15> or <16>, and the cancer treating method according to any one of <17> to <19> can solve the various problems in the related art and achieve the object of the present disclosure.

What is claimed is:
1. A neutron beam transmission adjusting device, comprising:
a neutron beam transmission unit that comprises a neutron reactant and is capable of modulating at least any one selected from the group consisting of an energy and a flux of a neutron beam transmitted through the neutron beam transmission unit,
wherein the neutron beam transmission unit contains a hydrogel containing water, a polymer, and a mineral.
2. The neutron beam transmission adjusting device according to claim 1,
wherein the neutron beam transmission adjusting device is used, with the neutron beam transmission adjusting device disposed between a source of the neutron beam and an irradiation target to be irradiated with the neutron beam on a path of the neutron beam, and
wherein the neutron beam transmission unit is configured to perform a modulation in an accordance with a lesion site condition of the irradiation target.
3. The neutron beam transmission adjusting device according to claim 2,
wherein the neutron beam transmission unit has a shape conforming to a surface of the irradiation target.
4. The neutron beam transmission adjusting device according to claim 1,
wherein the neutron reactant contains at least any one selected from the group consisting of a boron atom, a lithium atom, and a gadolinium atom.
5. The neutron beam transmission adjusting device according to claim 1,
wherein the neutron beam transmission unit has a thickness distribution.
6. The neutron beam transmission adjusting device according to claim 1,
wherein the neutron beam transmission unit has a concentration distribution of the neutron reactant.
7. The neutron beam transmission adjusting device according to claim 1,
wherein the neutron beam transmission unit is deformable.
8. A neutron beam adjusting method, comprising:
when irradiating an irradiation target of a neutron beam from a source of the neutron beam with the neutron beam, disposing the neutron beam transmission adjusting device according to claim 1 between the source of the neutron beam and the irradiation target of the neutron beam on a path of the neutron beam.
9. The neutron beam adjusting method according to claim 8, further comprising:
performing a modulation with the neutron beam transmission adjusting device in an accordance with a condition of the irradiation target of the neutron beam.

10. A method for producing a neutron beam transmission adjusting device, the method comprising:

producing a neutron beam transmission adjusting device according to claim 1 using a three-dimensional object producing apparatus.

11. The method for producing a neutron beam transmission adjusting device according to claim 10, wherein the three-dimensional object producing apparatus is a material jetting type.

12. The method for producing a neutron beam transmission adjusting device according to claim 10, wherein producing the neutron beam transmission adjusting device using the three-dimensional object producing apparatus comprising producing the neutron beam transmission adjusting device based on object formation data corresponding to a lesion site condition of an irradiation target to be irradiated with a neutron beam.

13. The method for producing a neutron beam transmission adjusting device according to claim 12, further comprising:

controlling a thickness distribution of the neutron beam transmission unit based on the object formation data.

14. The method for producing a neutron beam transmission adjusting device according to claim 12, further comprising:

controlling a concentration distribution of the neutron reactant in the neutron beam transmission unit based on the object formation data.

15. A cancer treating method, comprising:

using a neutron beam transmission adjusting device according to claim 1.

16. The cancer treating method according to claim 15, further comprising:

when irradiating an irradiation target of a neutron beam from a source of the neutron beam with the neutron beam, disposing the neutron beam transmission adjusting device between the source of the neutron beam and the irradiation target of the neutron beam on a path of the neutron beam.

17. The cancer treating method according to claim 15, further comprising:

performing a modulation using the neutron beam transmission adjusting device in an accordance with a lesion site condition of the irradiation target of the neutron beam.

* * * * *